United States Patent
Duong et al.

(12)

(10) Patent No.: US 6,620,963 B1
(45) Date of Patent: Sep. 16, 2003

(54) TRICYCLO[6.2.20$^{2,7}$]DODECA-2(7),3,5-TRIEN-4-CARBONYLAMINO-PHENYL AND TRICYCLO[6.2.20$^{2,7}$]DODECA-2(7),3,5-TRIEN-4-CARBONYLAMINO-HETEROARYL AND RELATED COMPOUNDS HAVING RARα RECEPTOR SELECTIVE BIOLOGICAL ACTIVITY

(75) Inventors: Tien T. Duong, Irvine, CA (US); Richard Beard, Newport Beach, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 25 days.

(21) Appl. No.: 10/246,896

(22) Filed: Sep. 19, 2002

(51) Int. Cl.$^7$ .................. C07C 69/78; C07C 229/40
(52) U.S. Cl. .................. 560/56; 544/224; 544/326; 544/336; 546/309; 548/110; 548/195; 548/233; 548/309; 548/331.1; 548/372.5; 549/4; 549/69; 549/480; 556/419; 562/455; 564/155; 564/180
(58) Field of Search .................. 544/224, 326; 544/336; 548/233, 331.1, 372.5, 195, 110; 546/309; 549/4, 69, 480; 556/419; 560/56; 562/45.5; 564/155, 180

(56) References Cited

U.S. PATENT DOCUMENTS

| | | |
|---|---|---|
| 5,037,825 A | 8/1991 | Klaus et al. |
| 5,420,145 A | 5/1995 | Shudo |
| 5,455,265 A | 10/1995 | Chandraratna |
| 5,523,457 A | 6/1996 | Starrett, Jr. et al. |
| 5,559,248 A | 9/1996 | Starrett, Jr. et al. |
| 5,648,385 A | 7/1997 | Starrett, Jr. et al. |
| 5,739,338 A | 4/1998 | Beard et al. |
| 5,760,276 A | 6/1998 | Beard et al. |
| 5,877,207 A | 3/1999 | Klein et al. |
| 5,965,606 A | 10/1999 | Teng et al. |
| 6,037,488 A | 3/2000 | Song et al. |
| 6,187,950 B1 | 2/2001 | Song et al. |
| 6,235,923 B1 | 5/2001 | Song et al. |
| 6,245,786 B1 | 6/2001 | Teng et al. |
| 6,252,090 B1 | 6/2001 | Vasudevan et al. |
| 6,342,602 B1 | 1/2002 | Teng et al. |
| 6,344,561 B2 | 2/2002 | Vuligonda et al. |
| 6,387,950 B2 | 5/2002 | Nehme et al. |

FOREIGN PATENT DOCUMENTS

| | | |
|---|---|---|
| EP | 91906248.9 | 4/1992 |
| EP | 93104626.2 | 9/1994 |
| EP | 95100032.2 | 7/1995 |
| EP | 95100033.0 | 7/1995 |
| EP | 95100032.2 | 5/1997 |
| WO | PCT/JP91/00350 | 4/1992 |
| WO | PCT/US92/11214 | 6/1993 |
| WO | WO-93-11755 | 6/1993 |
| WO | 95100032.2 | 7/1995 |

OTHER PUBLICATIONS

Allegretto, Elizabeth A., et al., *Transactivation Properties of Retinoic Acid and Retinoid X Receptors in Mammalian Cells and Yeast*, The Journal of Biological Chemistry, Issue of (Dec. 15, 1993), pp. 26625–26633, vol. 268, No. 35, © 1993 by The American Society for Biochemistry and Molecular Biology, Inc. U. S. A.

Chen, Claudia and Okayama, Hiroto, *High–Efficiency Transformation of Mammalian Cells by Plasmid DNA*, Molecular and Cellular Biology, (Aug. 1987), pp. 2745–2752, vol. 7, No. 8, © 1987, American Society for Microbiology.

Cheng, Yung–Chi and Prusoff, William H., *Relationship Between the Inhibition Constant ($K_1$) and the Concentration of Inhibitor Which Causes 50 Per Cent Inhibition ($I_{50}$) of an Enzymatic Reaction*, Biochemical Pharmacology, (1973), vol. 22, pp. 3099–3108, Pergamon Press, 1973, Printed in Great Britain.

Dawson and Okamura, William H., *V. Retinoid Structur–Biological Activity Relationships*, Chemistry and Biology of Synthetic Retinoids, (1990), pp. 324–356, published by CRC Press, Inc.

Eyrolles, Laurence, et al. *Retinobenzoic Acids. 6. Retinoid Antagonists with a Heterocyclic Ring*, J. Med. Chem., (May 13, 1994), vol. 37, No. 10, pp 1508–1517© 1994 by the American Chemical Society.

Felgner, Phillip L. and Holm, Marilyn, *Cationic Liposome–Method Transfection*, Focus, (Spring 1989), vol. 11, No. 2, pp. 21–24, published by Life Technologies, Inc.

Graupner, Gerhart, et al., *61Substituted Naphthalene–2 Carboxylic Acid analogs, A New Class of Retinoic Acid Receptor Subtype–Specific Ligands*, Biochemical and Biophysical Research Communications, (Sep. 30, 1991), vol. 179, No. 3, 1991, pp. 1554–1561, © 1991 by Academic Press, Inc.

Heyman, Richard A., et al., *9–Cis Retinoic Acid is a High Affinity Ligand for the Retinoid X Receptor*, Cell, (Jan. 24, 1992), vol. 68, pp. 397–406, © 1992 by Cell Press.

Kagechika, HiroYki, et al., *Affinity Gels for Purification of Retinoid–Specific Binding Protein (RSBP)*, Biochemical and Biophysical Research Communications, (Aug. 30, 1988), vol. 155, No. 1, 1988, pp. 503–508, © 1988 by Academic Press, Inc.

(List continued on next page.)

Primary Examiner—Joseph K. McKane
Assistant Examiner—Donna Wright
(74) Attorney, Agent, or Firm—Gabor L. Szekeres; Carlos A. Fisher; Martin A. Voet

(57) ABSTRACT

Compounds of the formula

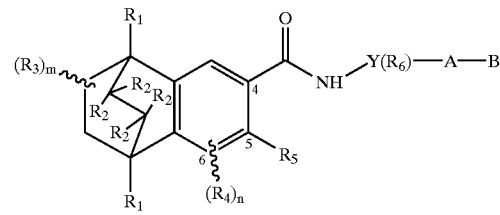

where the variables have the meaning defined in the specification, which bind specifically or selectively to to RARα retinoid receptors.

27 Claims, No Drawings

OTHER PUBLICATIONS

Kagechika, Hiroyki, et al., *Retinobenzoic Acids. 1. Structure–Activity Relationships of Aromatic Amides with Retinoidal Activity*, J. Med. Chem., (1988), vol. 31, pp. 2182–2192.

Klein, Elliott S., et al., *Identification and Functional Separation of Retinoic Acid Receptor Neutral Antagonists and Inverse Agonists*, The Journal of Biological Chemistry, (1996), vol. 271, No. 37, Issue of Sep. 13, pp. 22692–22696, Printed in U. S. A., © 1996 by The American Society for Biochemistry and Molecular Biology, Inc.

Mangelsdorf, David J., et al., *8/The Retinoid Receptors*, The Retinoids: Biology, chemistry and Medicine, $2^{nd}$ edition, pp. 319–349, Raven Press, Ltd., New York, © 1994.

Nagpal, Sunil, et al., *Separation of Transactivation and AP1 Antagonism Functions of Retinoic Acid Receptor α*, The Journal of Biological Chemistry, (1995), vol. 270, No. 2, issue of Jan. 13, pp. 923–927, 1995, © 1995 by The American Society for Biochemistry and Molecular Biology, Inc.

Standeven, Andrew M., et al., *Lack of Involvement of Retinoic Acid Receptor α in Retinoid–Induced Skin Irritation in Hairless Mice*, Elsevier Toxicology Letters 92 (1977), pp. 231–240, © 1997 Elsevier Science Ireland Ltd.

Sun, Shiyong, et al., *Inhibitory Effect of N–(41–Carboxypheny)–4–xHydroxy–3,5–Di–Tert–Butyl Benzamide on Chemically Induced Two–Stage Skin Papillomas in Mice*, Chemical Abstracts, (1992), vol. 117, p. 24.

Teng, Min, et al., *Identification of Highly Potent Retinoic Acid Receptor α–Selective Antagonists*, J. Med. Chem., (1997), vol. 40, pp. 2445–2451, © 1997 American Chemical Society.

Teng, Min, et al., *Identification of a Retinoic Acid Receptor α Subtype Specific Agonist*, J. Med. Chem. (Aug. 2, 1996), vol. 39, No. 16, pp. 3035–3038, © 1996 by the American Chemical Society.

Verma, A. K., and Boutwell, *Vitamin A Acid (Retinoic Acid), a Potent Inhibitor of 12–O–Tetradecanoyl–Phorbol–13–Acetate–Induced Ornithine Decarboxylase Activity in Mouse Epidermis*, Cancer Research, (Jul. 1977), vol. 37, pp. 2196–2201.

Allegretto, Elizabeth A., et al., *Transactivation Properties of Retinoic Acid and Retinoid X Receptors in Mammalian Cells and Yeast*, The Journal of Biological Chemistry, Issue of (Dec. 15, 1993), pp. 26625–26633, vol. 268, No. 35, © 1993 by The American Society for Biochemistry and Molecular Biology, Inc. U. S. A.

Chen, Claudia and Okayama, Hiroto, *High–Efficiency Transformation of Mammalian Cells by Plasmid DNA*, Molecular and Cellular Biology, (Aug. 1987), pp. 2745–2752, vol. 7, No. 8, © 1987, American Society for Microbiology.

Cheng, Yung–Chi and Prusoff, William H., *Relationship Between the Inhibition Constant ($K_1$) and the Concentration of Inhibitor Which Causes 50 Per Cent Inhibition ($I_{50}$) of an Enzymatic Reaction*, Biochemical Pharmacology, (1973), vol. 22, pp. 3099–3108, Pergamon Press, 1973, Printed in Great Britain.

Dawson and Okamura, William H., *V. Retinoid Structur–Biological Activity Relationships*, Chemistry and Biology of Synthetic Retinoids of Synthetic Retinoids, (1990), pp. 324–356, Pubished by CRC Press, Inc.

Eyrolles, Laurence, et al. *Retinobenzoic Acids. 6. Retinoid Antagonists with a Heterocyclic Ring*, J. Med. Chem., (May 13, 1994), vol. 37, No. 10, pp 1508–1517© 1994 by the American Chemical Society.

Felgner, Phillip L. and Holm, Marilyn, *Cationic Liposome–Method Transfection*, Focus, (Spring 1989), vol. 11, No. 2, pp. 21–24, published by Life Technologies, Inc.

Graupner, Gerhart, et al., *61–Substituted Naphthalene–2 Carboxylic Acid analogs, A New Class of Retinoic Acid Receptor Subtype–Specific Ligands*, Biochemical and Biophysical Research Communications, (Sep. 30, 1991), vol. 179, No. 3, 1991, pp. 1554–1561, © 1991 by Academic Press, Inc.

Heyman, Richard A., et al., *9–Cis Retinoic Acid is a High Affinity Ligand for the Retinoid X Receptor*, Cell, (Jan. 24, 1992), vol. 68, pp. 397–406, © 1992 by Cell Press.

Kagechika, Hiroyki, et al., *Affinity Gels for Purification of Retinoid–Specific Binding Protein (RSBP)*, Biochemical and Biophysical Research Communications, (Aug. 30, 1988), vol. 155, No. 1, 1988, pp. 503–508, © 1988 by Academic Press, Inc.

Kagechika, Hiroyki, et al., *Retinobenzoic Acids. 1. Structure–Activity Relationships of Aromatic Amides with Retinoidal Activity*, J. Med. Chem., (1988), vol. 31, pp. 2182–2192.

Klein, Elliott S., et al., *Identification and Functional Separation of Retinoic Acid Receptor Neutral Antagonists and Inverse Agonists*, The Journal of Biological Chemistry, (1996), vol. 271, No. 37, Issue of Sep. 13, pp. 22692–22696, Printed in U. S. A., © 1996 by The American Society for Biochemistry and Molecular Biology, Inc.

Mangelsdorf, David J., et al., *8/The Retinoid Receptors*, The Retinoids: Biology, chemistry and Medicine, $2^{nd}$ edition, pp. 319–349, Raven Press, Ltd., New York, © 1994.

Nagpal, Sunil, et al., *Separation of Transactivation and AP1 Antagonism Functions of Retinoic Acid Receptor α*, The Journal of Biological Chemistry, (1995), vol. 270, No. 2, issue of Jan. 13, pp. 923–927, 1995, © 1995 by The American Society for Biochemistry and Molecular Biology, Inc.

Standeven, Andrew M., et al., *Lack of Involvement of Retinoic Acid Receptor α in Retinoid–Induced Skin Irritation in Hairless Mice*, Elsevier Toxicology Letters 92 (1977), pp. 231–240, © 1997 Elsevier Science Ireland Ltd.

Sun, Shiyong, et al., *Inhibitory Effect of N–(41–Carboxypheny)–4–xHydroxy–3,5–Di–Tert–Butyl Benzamide on Chemically Induced Two–Stage Skin Papillomas in Mice*, Chemical Abstracts, (1992), vol. 117, p. 24.

Teng, Min, et al., *Identification of Highly Potent Retinoic Acid Receptor α–Selective Antagonists*, J. Med. Chem., (1997), vol. 40, pp. 2445–2451, © 1997 American Chemical Society.

Teng, Min, et al., *Identification of a Retinoic Acid Receptor α Subtype Specific Agonist*, J. Med. Chem. (Aug. 2, 1996), vol. 39, No. 16, pp. 3035–3038, © 1996 by the American Chemical Society.

Verma, A. K., and Boutwell, *Vitamin A Acid (Retinoic Acid(, a Potent Inhibitor of 12–O–Tetradecanoyl–Phorbol–13–Acetate–Induced Ornithine Decarboxylase Activity in Mouse Epidermis*, Cancer Research, (Jul. 1977), vol. 37, pp. 2196–2201.

TRICYCLO[6.2.20$^{2,7}$]DODECA-2(7),3,5-TRIEN-4-CARBONYLAMINO-PHENYL AND TRICYCLO[6.2.20$^{2,7}$]DODECA-2(7),3,5-TRIEN-4-CARBONYLAMINO-HETEROARYL AND RELATED COMPOUNDS HAVING RARα RECEPTOR SELECTIVE BIOLOGICAL ACTIVITY

BACKGROUND OF THE INVENTION

1. Field of the Invention

The present invention relates to novel compounds having retinoid-like biological activity. More specifically, the present invention relates to tricyclo[6.2.20$^{2,7}$]dodeca-2(7), 3,5-trien-4-carbonyl)amino]-phenyl and tricyclo[6.2.20$^{2,7}$] dodeca-2(7),3,5-trien-4-carbonyl)amino]-heteroaryl and related compounds having RARα receptor selective biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

It is now general knowledge in the art that two main types of retinoid receptors exist in mammals (and other organisms). The two main types or families of receptors are respectively designated the RARs and RXRs. Within each type there are subtypes; in the RAR family the subtypes are designated RARα, RARβ and RARγ, in RXR the subtypes are: RXRα, RXRβ and RXRγ. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes.

Recently, a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists. U.S. Pat. No. 5,877,207 titled "Synthesis and Use of Retinoid Compounds Having Negative Hormone and/or Antagonist Activities" describes the foregoing two-state model and the use of retinoid antagonist and negative hormones in detail.

Among the scientific publications Dawson and William H. Okamura, *Chemistry and Biology of Synthetic Retinoids*, published by CRC Press Inc., 1990, pages 334–335, 354 and 324–356 is of special interest as an overview of the prior art on the subject.

The following is a list of United States and foreign patents and publications which disclose compounds having structural similarity to the compounds of the present invention, or disclose compounds having RARα selective agonist-like activity: U.S. Pat. Nos. 6,235,923; 6,245,786; 6,252,090; 6,342,602; 6,344,561; 6,387,950; 5,965,606; 6,037,488; 6,037,488; 6,187,950; 5,739,338; 5,760,276; 5,037,825; 5,420,145; 5,523,457; 5,559,248; 5,648,385; EPO 0 478 787; EPO 0 617 020; EPO 0 661 259; EPO 0 661 261; Eyrolles et al. J. Med. Chem. 1994 37 pp 1508–1517; Graupner et al. Biochem. Biophys. Res. Commun. 179 1991 pp 1554–1561; Kagechika et al. Biochem. Biophys. Res. Commun. 155 1988 pp 503–508; Kagechika et al. J. Med. Chem. 1988 31 pp 2182–2192; Standeven et al. Toxicology Letters 92 (1997) pp 231–240; Chem. Abstracts 117 (1992) 117:124091j; Teng et al. J. Med. Chem. 1997 40 pp 2445–2451; Teng et al. J. Med. Chem. 1996 39 pp 3035–3038; Nagpal et al. J. of Biol. Chem. 270 (1995) pp 923–927.

SUMMARY OF INVENTION

The present invention relates to compounds of Formula 1

Formula 1

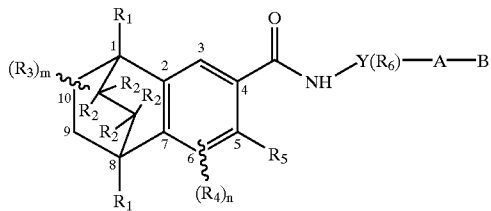

where $R_1$ is independently H, or alkyl of 1 to 6 carbons;

$R_2$ is independently H, or alkyl of 1 to 6 carbons;

$R_3$ is alkyl of 1 to 6 carbons, or halogen;

m is an integer having the values of 0 to 4;

$R_4$ independently is alkyl of 1 to 6 carbons or halogen;

n is an integer having the values of 0 to 2;

$R_5$ is H or OH;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_6$ groups;

$R_6$ is halogen, alkyl of 1 to 10 carbons, fluoro substituted alkyl of 1 to 6 carbons, alkoxy of 1 to 10 carbons, or alkylthio of 1 to 10 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, $COOR_8$, $CONR_9R_{10}$, $-CH_{2l\ OH}$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, or $CH_2OCH_3$, or $R_8$ is phenyl or $C_{1-6}$ alkylphenyl, $R_9$ and $R_{10}$ independently are hydrogen, an alkyl group of 1 to 10 carbons, or a cycloalkyl group of 5–10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2–5 carbons, or a pharmaceutically acceptable salt of said compound.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of metabolic diseases such as type II diabetes and diabetes mellitus and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as $Minoxidil^R$, diseases associated with the immune system, including use of the present compounds as immunosuppressants and immunostimulants, modulation of organ transplant rejection and facilitation of wound healing, including modulation of chelosis.

Generally speaking, the second aspect of the invention relates to the use of the novel compounds to prevent or treat diseases and conditions which are responsive to compounds that promote the expression of or bind to receptors belonging to the steroid or thyroid receptor superfamily.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids.

BIOLOGICAL ACTIVITY, MODES OF ADMINISTRATION

Assays of Retinoid-like Biological Activity

A classic measure of retinoic acid activity involves measuring the effects of retinoic acid on ornithine decarboxylase. The original work on the correlation between retinoic acid and a decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to RARα, RARβ, RARγ, RXRα, RXRβ and RXRγ receptors, and the ability or inability of the compounds to activate transcription of a reporter gene through these receptor subtypes can be tested. Because of the complex distribution of the different retinoid receptors in various organs of the mammalian body agonists of only one or two receptor subtypes may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the RARα, RARβ, RARγ, RXRα receptor subtypes, and which is based on work published by Feigner P. L. and Holm M (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

CV-1 cells ($4 \times 10^5$ cells/well) were transiently transfected with the luciferase reporter plasmid MTV4(R5G)-Luc (0.7 ug/well) containing four copies of the R5G retinoid DNA response element along with the RXRα expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 μl instead of 100 μl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean+SEM of triplicate determinations normalized to β-galactosidase activity.

Table 1 discloses the activity of certain exemplary compounds of the invention in the above-described ligand binding assay. Table 1 also discloses three of the most preferred compounds of the invention, shown in their free carboxylic acid form. As it can be seen from Table 1, the compounds of the invention bind specifically or selectively to RARα retinoid receptors.

TABLE 1

| compound number | structure | RAR $K_d$ (nM) | | |
|---|---|---|---|---|
| | | α | β | γ |
| 8 | [chemical structure] | 53 | 7.2K | >10K |

TABLE 1-continued

| compound number | structure | RAR K$_d$ (nM) | | |
|---|---|---|---|---|
| | | α | β | γ |
| 10 | 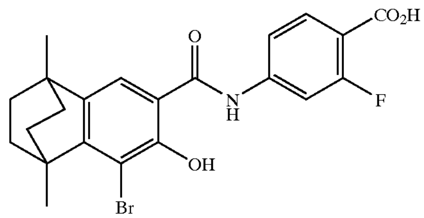 | 32 | >10K | >10K |
| 14 | 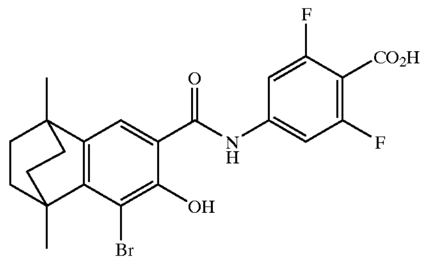 | 84 | >10K | >10K |

Modes of Administration

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

GENERAL EMBODIMENTS AND SYNTHETIC METHODOLOGY

Definitions

The term alkyl refers to and covers any and all groups which are known as normal alkyl, branched-chain alkyl, cycloalkyl and also cycloalkyl-alkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH; this term covers compounds derived from organic acids capable of forming esters including phosphorous based and sulfur based acids, or compounds of the formula —CH$_2$OCOR$_{11}$ where R$_{11}$ is a variable as defined above in connection with Formula 1.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

The term amide has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono-and disubstituted amides derived from the substituted and unsubstituted phenyl or lower alkylphenyl amines. Unsubstituted amides are also preferred.

Acetals and ketals include the radicals of the formula —CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfiric acid or phosphoric acid. Any of a number of simple organic acids such as mono-, di- or tri-acid may also be used.

The compounds of the present invention are capable of existing as trans and cis (E and Z) isomers relative to olephinic double bonds, cycloalkyl rings provided one or more olephinic bonds and/or one or more cycloalkyl ring is present in the compound. The invention covers trans as well as cis isomers relative to each center that gives rise to such isomerism, as well as mixture of such isomers. The compounds of the present invention may and typically do contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

Generally speaking the compounds of the invention can be obtained by the reactions illustrated in Reaction Scheme 1. The starting material in this scheme is a cyclohexane derivative of Formula 2, which already has the R$_1$, R$_2$ and R$_3$ substituents, where the variables R$_1$, R$_2$ and R$_3$ are defined as in connection with Formula 1. Such substituted cyclohexane derivatives can be obtained in accordance with the chemical scientific and/or patent literature, or in accordance with such modification of the scientific and/or patent literature which is readily apparent to those skilled in the art. An example of a compound of Formula 2 is 1,4 dimethyl-cyclohexane which is used as a starting material in the synthesis of several preferred compounds of the invention. 1,4-Dimethylcyclohexane is available from Aldrich Chemical Company, Inc (Aldrich). The cyclohexane derivative of Formula 2 is reacted with tertiary-butyl chloride in the presence of aluminum chloride (AlCl$_3$) to provide the 2,4-dichlorinated cyclohexane derivative of Formula 3. The 2,4-dichlorinated cyclohexane derivative of Formula 3 is then reacted with a benzene derivative of Formula 4 in the presence of aluminum chloride. Although Reaction Scheme 1 illustrates the synthesis of compounds of the invention where the group corresponding to the R$_5$ group of Formula 1 is OH (a phenol derivative) it will be readily apparent to those skilled in the art that the synthesis of such compounds of the invention where the variable R$_5$ represents hydrogen can also be performed in accordance with scheme with only such modification of the scheme which will become readily apparent to those skilled in the art.

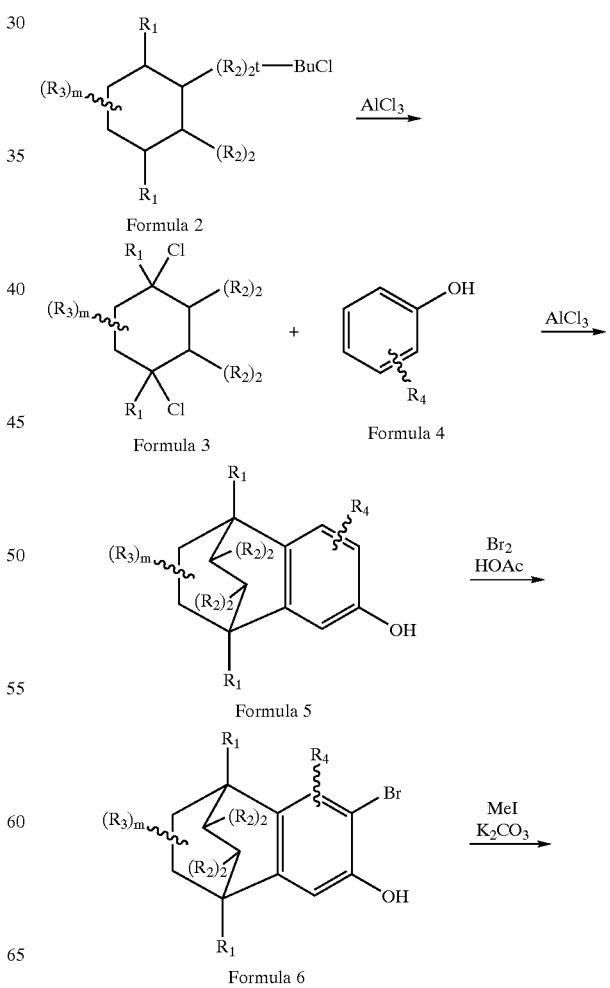

Reaction Scheme 1

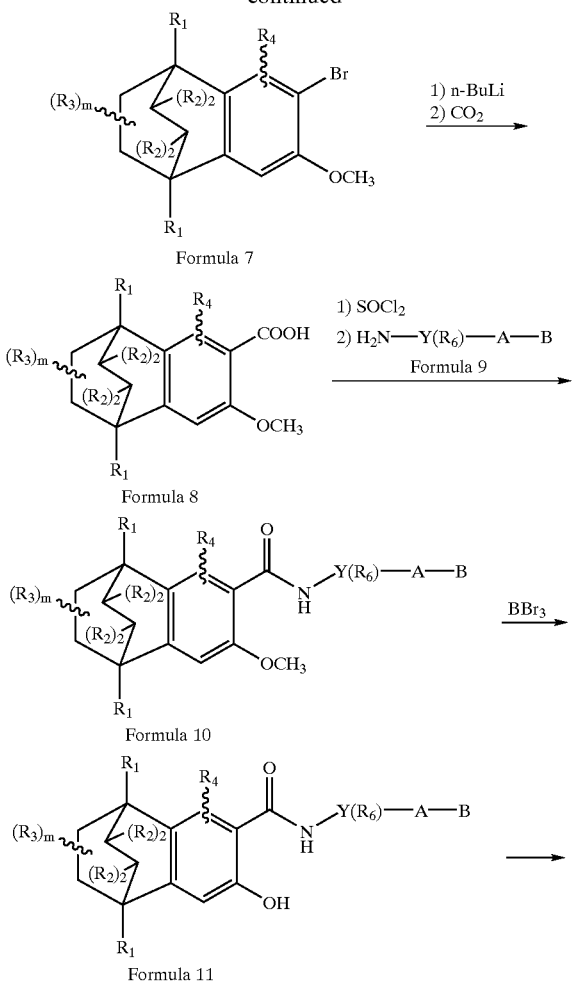

Formula 7

Formula 8

Formula 10

Formula 11

ANALOGS AND DERIVATIVES

The product of this Friedel Crafts type reaction is a spiro compound of Formula 5, which is then brominated to provide a bromo derivative Spiro compound of Formula 6. The phenolic hydroxyl group of the bromo spiro compound of Formula 6 is protected with a methyl group as a result of reaction with methyl iodide in the presence of base, such as potassium carbonate, to yield the bromo-methoxy Spiro compound of Formula 7. The bromo-methoxy spiro compound of Formula 7 is then reacted with strong base, such as normal butyl lithium, and carbon dioxide, to "capture" carbon dioxide and provide the Spiro carboxylic acid derivative of Formula 8. The spiro carboxylic acid derivative of Formula 8 is first reacted with thionyl chloride to provide the corresponding acid chloride, and thereafter with an amino-aryl- or amino-heteroaryl compound of Formula 9 in a basic solvent, such as pyridine. Examples of reagents of Formula 9 are ethyl 4-aminobenzoate, ethyl 4-amino-2-fluorobenzoate, ethyl-4-amino-2,4-difluorobenzoate, ethyl 2-amino-pyridine-5-carboxylate, ethyl 2-amino-pyridine-4-carboxylate, ethyl 2-amino thiophene-4-carboxylate, ethyl 2-amino thiophene-5-carboxylate, ethyl 2-amino furan-4-carboxylate and ethyl 2-amino furan-5-carboxylate. Ethyl 4-aminobenzoate is available from Aldrich, ethyl 4-amino-2-fluorobenzoate and ethyl-4-amino-2,4-difluorobenzoate can be obtained in accordance with the synthetic procedures described in U.S. Pat. No. 5,663,357, incorporated herein by reference. Generally speaking, the compounds of Formula 9 can be obtained in accordance with the chemical scientific and/or patent literature, or in accordance with such modification of the scientific and/or patent literature which is readily apparent to those skilled in the art.

The reaction of the carboxylic acid chloride made from the spiro carboxylic acid derivative of Formula 8 with the amino-aryl- or amino-heteroaryl compound of Formula 9 yields the spiro amide compound of Formula 10. The methyl protecting group from the phenolic hydroxyl of the compound of Formula 10 is then removed by treatment of boron triboromide ($BBr_3$) in an anhydrous aprotic solvent, such as methylene dichloride. The resulting spiro-amide compound of Formula 11 is a compound of the invention, within the scope of Formula 1. The compound of Formula 11 can be converted into further compounds of the invention within the scope of Formula 1 by such reactions as esterification, saponification, homologation, reduction to aldehyde or alcohol stage and the like, which per se are well known in the art. These reactions usually involve transformations of the group B in Formula 1 but are not necessarily limited to those. For some of the compounds of the invention these transformations are preferably performed on the intermediate of Formula 10, rather than on the compound of Formula 11. Some of the known and published general principles and synthetic methodology employed in the transformations of the B group are briefly described below.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (MAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 14 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Acetals or ketals can be prepared from the corresponding aldehyde or ketone by the method described in March, ibid, p 810.

SPECIFIC EMBODIMENTS

With reference to the symbol Y in Formula 1 the preferred compounds of the invention are those where Y is phenyl. Compounds are also preferred where Y is a bivalent naphthyl, pyridyl, thienyl or furyl radical. When Y is phenyl, the compounds are generally preferred with the phenyl radical being 1,4 (para) substituted with the carbamoyl (amide) and A—B groups. When Y is pyridyl, the compounds are generally preferred with the pyridyl group being 2,5 substituted with the carbamoyl (amide) and A—B groups. When Y is phenyl, compounds are also preferred with an $R_6$ substituent in the ortho, and/or ortho and ortho' positions relative to the A—B group.

The $R_1$ group in the preferred compounds of the invention is H or alkyl of 1 to 3 carbons. Even more preferably $R_1$ is methyl. $R_2$ is preferably H or lower alkyl 1 to 3 carbons, and even more preferably $R_2$ is hydrogen.

The non-aromatic portion of the condensed spiro moiety of the compounds of the invention is preferably not substituted with an $R_3$ group, that is the variable m is preferably zero (0).

The aromatic portion of the condensed spiro moiety of the compounds of the invention is preferably not substituted with an $R_4$ group, that is the variable n is preferably zero (0). Alternatively and just as preferably, n is one (1), the $R_4$ group is halogen, preferably bromine, and the $R_4$ group is in the 6-position of the condensed Spiro moiety. The numbering of the condensed Spiro moiety is indicated in Formula 1.

The variable $R_5$ is H or OH, preferably OH. In some preferred compounds of the invention there is no optional variable $R_6$, that is the aryl or heteroaryl ring is not substituted with an $R_6$ group. In other preferred compounds of the invention the $R_6$ group is preferably halogen, alkyl of 1 to 3 carbons, fluoro substituted alkyl of 1 to 3 carbons, alkoxy of 1 to 3 carbons, or alkylthio of 1 to 3 carbons. Among the halogens, the fluoro (F) substituent is preferred.

The presently most preferred compounds of the invention are shown as free carboxylic acids in Table 2, with reference to Formula 12, however it should be kept in mind that pharmaceutically acceptable salts and $C_{1-6}$ alkyl esters, particularly ethyl and methyl esters of these compounds are also preferred.

Formula 12

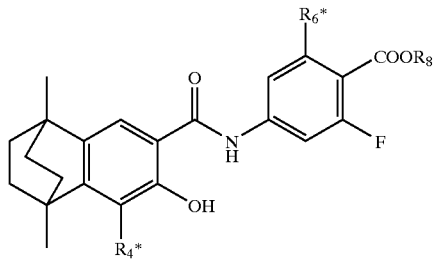

TABLE 2

| Compound # | $R_4{}^*$ | $R_6{}^*$ |
|---|---|---|
| 8 | H | H |
| 10 | Br | H |
| 14 | Br | F |

SPECIFIC EXAMPLES

Reaction Scheme 2 illustrates the presently preferred synthetic steps in which the presently most preferred compounds of the invention are obtained. A detailed description of the experimental procedures of these synthetic steps is also provided below.

1,4-Dichloro-1,4-dimethylcyclohexane (Compound 1)

To a solution of 1,4-dimethylcyclohexane (10 g, 89.1 mmol) and tert-butyl chloride (32.6 g, 348 mmol) in 45 mL of anhydrous methylene chloride in a 3-neck round-bottom flask under argon at 0° C., was slowly added aluminum chloride (1.24 g, 8.91 mmol). The resulting mixture was stirred at 0° C. for 1.5 hours then quenched with ice, and the product was extracted with $CH_2Cl_2$. The organic layer was separated and washed with water, and brine, and dried over $Na_2SO_4$, and filtered, and concentrated under reduced pressure. The residue was purified by Kugelrohr distillation to yield the title compound as a pale yellow liquid.

$^1$H NMR (300 MHz, $CDCl_3$) δ 1.90 (m, 8H), 1.60 (s, 6H).

Reaction Scheme 2

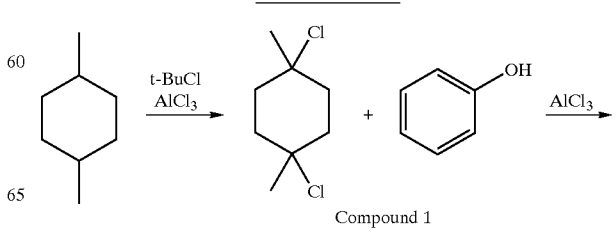

Compound 1

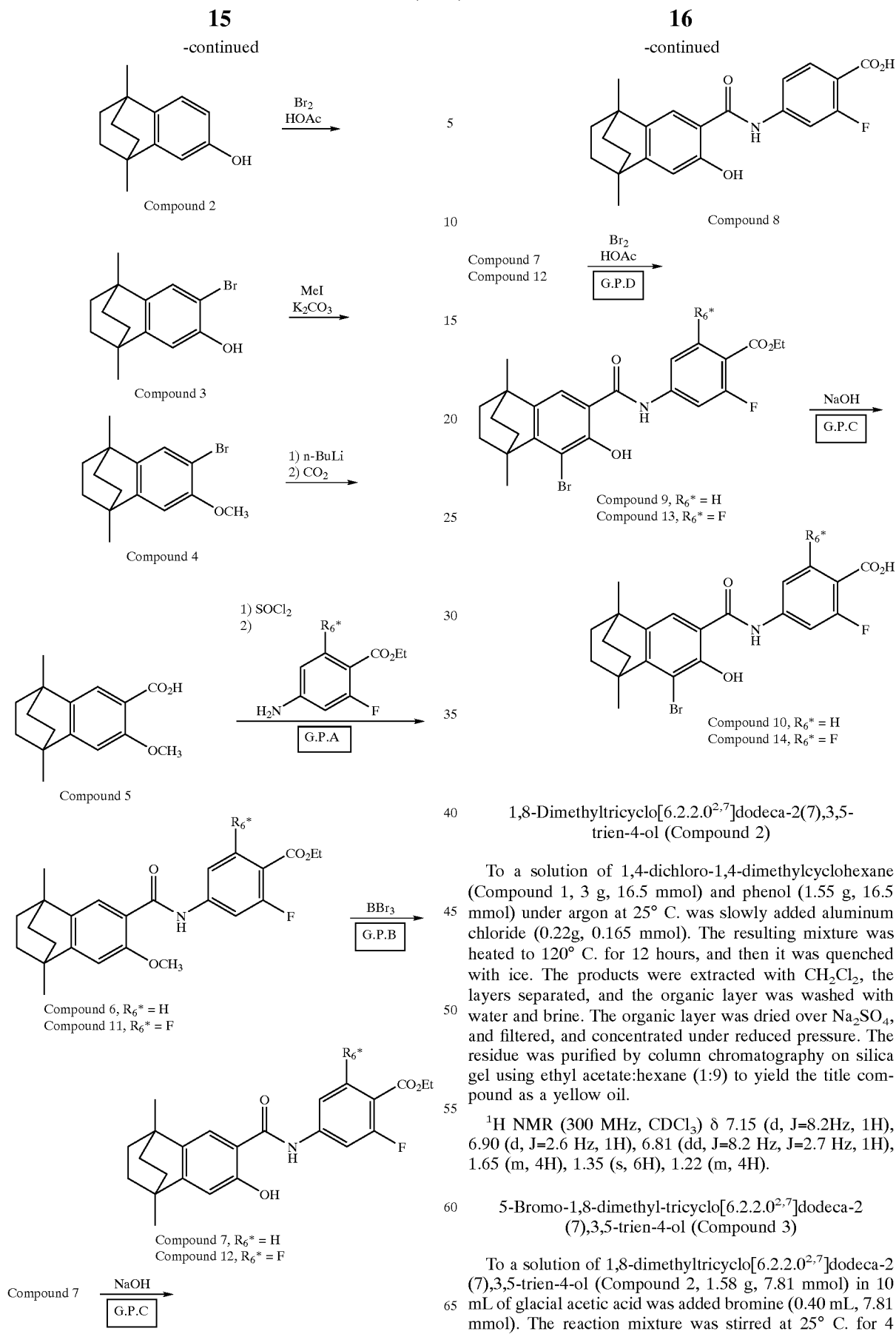

1,8-Dimethyltricyclo[6.2.2.0$^{2,7}$]dodeca-2(7),3,5-trien-4-ol (Compound 2)

To a solution of 1,4-dichloro-1,4-dimethylcyclohexane (Compound 1, 3 g, 16.5 mmol) and phenol (1.55 g, 16.5 mmol) under argon at 25° C. was slowly added aluminum chloride (0.22g, 0.165 mmol). The resulting mixture was heated to 120° C. for 12 hours, and then it was quenched with ice. The products were extracted with CH$_2$Cl$_2$, the layers separated, and the organic layer was washed with water and brine. The organic layer was dried over Na$_2$SO$_4$, and filtered, and concentrated under reduced pressure. The residue was purified by column chromatography on silica gel using ethyl acetate:hexane (1:9) to yield the title compound as a yellow oil.

$^1$H NMR (300 MHz, CDCl$_3$) δ 7.15 (d, J=8.2Hz, 1H), 6.90 (d, J=2.6 Hz, 1H), 6.81 (dd, J=8.2 Hz, J=2.7 Hz, 1H), 1.65 (m, 4H), 1.35 (s, 6H), 1.22 (m, 4H).

5-Bromo-1,8-dimethyl-tricyclo[6.2.2.0$^{2,7}$]dodeca-2(7),3,5-trien-4-ol (Compound 3)

To a solution of 1,8-dimethyltricyclo[6.2.2.0$^{2,7}$]dodeca-2(7),3,5-trien-4-ol (Compound 2, 1.58 g, 7.81 mmol) in 10 mL of glacial acetic acid was added bromine (0.40 mL, 7.81 mmol). The reaction mixture was stirred at 25° C. for 4 hours then quenched with 10% Na$_2$S$_2$O$_3$ and extracted with Et$_2$O. The combined ether extracts were washed with water and brine, and dried over Na$_2$SO$_4$, and filtered, and concentrated under reduced pressure. The residue was purified by column chromatography on silica gel using ethyl acetate::hexane (2:98) to yield the title compound as a yellow oil.

$^1$H NMR (300 MHz, CDCl$_3$) δ 7.25 (s, 1H), 6.92 (s, 1H), 5.38 (s, OH), 1.65 (m, 4H), 1.35 (s, 6H), 1.22 (m, 4H).

4-Bromo-5-methoxy-1,8-dimethyl-tricyclo [6.2.2.0$^{2,7}$]dodeca-2(7),3,5-triene (Compound 4)

To a solution of 5-bromo-1,8-dimethyl-tricyclo[6.2.2.0$^{2,7}$]dodeca-2(7),3,5-trien-4-ol (Compound 3, 0.825 g, 2.94 mmol) in 10 mL of anhydrous acetone was added potassium carbonate (0.128 g, 8.82 mmol) and iodomethane (0.1 mL, 8.82 mmol). The reaction mixture was stirred at 25° C. for 12 hours and filtered. The filtrate was concentrated, and then it was diluted with ether and washed with water and brine. The organic layer was dried over Na$_2$SO$_4$, and filtered, and concentrated under reduced pressure. The residue was purified by column chromatography on silica gel using ethyl acetate:hexane (5:95) to yield the title compound as a white solid.

$^1$H NMR (300 MHz, CDCl$_3$) δ 7.34 (s, 1H), 6.81 (s, 1H), 3.92 (s, 3H), 1.65 (m, 4H), 1.38 (s, 3H), 1.36 (s, 3H), 1.22 (m, 4H).

5-Methoxy-1,8-dimethyl-tricyclo[6.2.2.0$^{2,7}$]dodeca-2(7),3.5-triene-4-carboxylic Acid (Compound 5)

To a solution of 4-bromo-5-methoxy-1,8-dimethyl-tricyclo[6.2.2.0$^{2,7}$]dodeca-2(7),3,5-triene (Compound 4, 779 mg, 2.65 mmol) and 20 mL of anhydrous THF under argon at −78° C. was slowly added tert-butyl lithium (3.43 mL, 5.82 mmol). The resulting mixture was stirred at −78° C. for 1 hour and CO$_2$ gas was bubbled into mixture for 45 minutes. The reaction was then stirred under argon for 15 minutes at −78° C. and then quenched by adding 10% HCl (10 mL). The product was extracted with EtOAc and the crude extract was washed with water and brine, and dried over Na$_2$SO$_4$. The solution was filtered and concentrated in vacuo. The residue was purified by column chromatography using ethyl acetate:hexane (1:9) followed by pure ethyl acetate to yield the title compound as a white solid.

$^1$H NMR (300 MHz, CDCl$_3$) δ 7.98 (s, 1H), 6.93 (s, 1H), 4.12 (s, 3H), 1.70 (m, 4H), 1.43 (s, 3H), 1.42 (s, 3H), 1.25 (m, 4H).

Ethel 2-Fluoro-4-[(5-methoxy-1,8-dimethyl-tricyclo [6.2.2.0$^{2,7}$]dodeca-2(7),3,5-triene-4-carbonyl)amino] benzoate (Compound 6) General Procedure A (G. P. A)

A solution of 5-methoxy-1,8-dimethyl-tricyclo[6.2.2.0$^{2,7}$]dodeca-2(7),3,5-triene-4-carboxylic acid (Compound 5, 142 mg, 0.55 mmol) and 2 ml of thionyl chloride was heated to reflux for 2 hours. The solution was concentrated under reduced pressure, and the residue was dissolved in CH$_2$Cl$_2$ (5ml). The solution was treated with ethyl 4-amino-2-fluorobenzoate (see U.S. Pat. No. 5,663,357, 100 mg, 0.55 mmol) and pyridine (2 mL). The resulting mixture was stirred at room temperature for 2 hours and then diluted with EtOAc and water. The layers were separated and the organic layer was washed with brine, and dried over Na$_2$SO$_4$, and filtered, and concentrated in vacuo. The residue was purified by column chromatography on silica gel using ethyl acetate::hexane (1:9) to yield the title compound as a white solid.

$^1$H NMR (300 MHz, CDCl$_3$) δ 10.12 (s, NH), 8.08 (s, 1H), 7.95 (t, J=8.4 Hz, 1H), 7.80 (dd, J=12.0 Hz, J=2.1 Hz, 1H), 7.32 (dd, J=6.5 Hz, J=2.1 Hz, 1H), 6.91 (s, 1H), 4.39 (q, J=7.2 Hz, 2H), 4.11 (s, 3H), 1.70 (m, 4H), 1.46 (s, 3H), 1.43 (s, 3H), 1.49 (t, J=7.0 Hz, 3H,), 1.25 (m, 4H).

Ethyl 2-Fluoro-4-[(5-hydroxy-1,8-dimethyl-tricyclo [6.2.20$^{2,7}$]dodeca-2(7),3,5-trien-4-carbonyl)amino] benzoate (Compound 7) General Procedure B (G. P. B.)

To a solution of ethyl 2-fluoro-4-[(5-methoxy-1,8-dimethyl-tricyclo[6.2.2.0$^{2,7}$]dodeca-2(7),3,5-triene-4-carbonyl)amino]benzoate (Compound 6, 133 mg, 0.31 mmol) and 10 mL of anhydrous CH$_2$Cl$_2$ under argon at −78° C. was slowly added boron tribromide (0.47 mL, 0.47 mmol). The resulting mixture was stirred at −78° C. to 25° C. for 12 hours, and then the reaction was quenched with ice. The product was extracted with EtOAc, the layers were separated, and the organic layer was washed with water, and brine, and dried over Na$_2$SO$_4$, filtered, and concentrated under reduced pressure. The residue was purified by column chromatography on silica gel using ethyl acetate:hexane (1:9) to yield the title compound as a white solid.

$^1$H NMR CDCl$_3$ δ 8.09 (bs, 1H), 7.95 (t, J=8.3 Hz, 1H), 7.72 (dd, J=12.0 Hz, J=2.1 Hz, 1H), 7.33 (dd, J=6.5 Hz, J=2.2 Hz, 1H), 7.19 (s, 1H), 6.92 (s, 1H), 4.39 (q, J=7.2 Hz, 2H), 1.71 (m, 4H), 1.46 (s, 3H), 1.43 (s, 3H), 1.48 (t, J=7.0 Hz, 3H), 1.25 (m, 4H).

2-Fluoro-4-[(5-hydroxy-1,8-dimethyl-tricyclo [6.2.20$^{2,7}$]dodeca-2(7),3,5-trien-4-carbonyl)amino] benzoic Acid (Compound 8) General Procedure C (G. P. C.)

To a solution of ethyl 2-fluoro-4-[(5-hydroxy-1,8-dimethyl-tricyclo[6.2.20$^{2,7}$]dodeca-2(7),3,5-trien-4-carbonyl)amino]benzoate (Compound 7, 23 mg, 0.06 mmol) in 2 mL of EtOH and 1 mL of THF was added 1 mL of 2 M NaOH(aq). The reaction mixture was stirred at room temperature for 12 hours, and then it was acidified with 10% HCl to pH=5. The excess alcohol was removed by rotary evaporation and the aqueous layer was extracted with ethyl acetate (3×10 mL). The combined organic layers were washed with water, and brine, and dried over Na$_2$SO$_4$. The crude acid was recrystallized from acetonitrile to produce the title compound (free carboxylic acid) as a white solid.

$^1$H NMR (300 MHz, acetone-d$_6$) δ 10.17 (bs, 1H), 7.95 (t, J=8.5 Hz, 1H), 7.85 (dd, J=11.4 Hz, J=2.1 Hz, 1H), 7.73 (s, 1H), 7.54 (dd, J=6.5 Hz, J=2.0 Hz, 1H), 6.82 (s, 1H), 1.71 (m, 4H), 1.36 (s, 3H), 1.34 (s, 3H), 1.25 (m, 4H).

Ethyl 4-[(6-Bromo-5-hydroxy-1,8-dimethyl-tricyclo [6.2.20$^{2,7}$]dodeca-2(7),3,5-trien-4-carbonylamino]-2-fluorobenzoate (Compound 9) General Procedure D (G. P. D. )

To a solution of ethyl 2-fluoro-4-[(5-hydroxy-1,8-dimethyl-tricyclo[6.2.20$^{2,7}$]dodeca-2(7),3,5-trien-4-carbonyl)amino]benzoate (Compound 7, 93 mg, 0.23 mmol) and 6 mL of dry carbon tetrachloride was added bromine (0.012 mL, 0.23 mmol). The reaction mixture was stirred at 25° C. for 12 hours, and then it was quenched with 10% aqueous Na$_2$S$_2$O$_3$. The product was extracted with Et$_2$O, and the combined organic layers were washed with water and brine. The ether extract was dried over Na$_2$SO$_4$, and filtered, and concentrated in vacuo. The residue was purified by column chromatography on silica gel using ethyl acetate::hexane (1:9) to yield the title compound as a white solid.

$^1$H NMR (300 MHz, CDCl$_3$) δ 10.27 (s, 1H), 8.93 (bs, 1H), 7.95 (t, J=8.3 Hz, 1H), 7.76 (dd, J=1.0 Hz, J=2.0 Hz,

1H), 7.56 (s, 1H), 7.34 (dd, J=6.5 Hz, J=1.9 Hz, 1H), 4.39 (q, J=7.2 Hz, 2H), 1.80 (s, 3H), 1.65 (m, 4H), 1.43 (s, 3H), 1.41 (t, J=7.0 Hz, 3H), 1.25 (m, 4H).

4-[(6-Bromo-5-hydroxy-1,8-dimethyl-tricyclo[6.2.20$^{2,7}$]dodeca-2(7),3,5-trien-4-carbonyl)amino]-2-fluorobenzoic Acid (Compound 10)

Following General Procedure C, ethyl 4-[(6-bromo-5-hydroxy-1,8-dimethyl-tricyclo[6.2.20$^{2,7}$]dodeca-2(7),3,5-trien-4-carbonyl)amino]-2-fluorobenzoate (Compound 9, 67 mg, 0.14 mmol) and 2 M NaOH (aq) (2 mL) were reacted to yield the title compound as a white solid.

$^{1}$H NMR (300 MHz, aectone-d$_6$) δ 12.78 (s, 1H), 10.23 (s, 1H), 7.98 (t, J=8.4 Hz, 1H), 7.80 (dd, J=11.0 Hz, J=2.0 Hz, 1H), 7.75 (s, 1H), 7.56 (dd, J=6.6 Hz, J=1.7 Hz, 1H), 1.77 (s, 3H), 1.60 (m, 4H), 1.38 (s, 3H), 1.20 (m, 4H).

Ethyl 2,6-Difluoro-4-[(5-methoxyy-1,8-dimethyl-tricyclo[6.2.2.0$^{2,7}$]dodeca-2(7),3,5-triene-4-carbonyl)amino]benzoate (Compound 11)

Following General Procedure A 5-methoxy-1,8-dimethyl-tricyclo[6.2.2.0$^{2,7}$]dodeca-2(7),3,5-triene-4-carboxylic acid (Compound 5, 39mg, 0.53mmol) and ethyl 2,6-difluoro-4-aminobenzoate (see U.S. Pat. No. 5,663,357, 107 mg, 0.53 mmol) were reacted to produce the title compound as a white solid.

$^{1}$H NMR (300 MHz, CDCl$_3$) δ 10.18 (s, NH), 8.07 (s, 1H), 7.41 (s, 1H), 7.38 (s, 1H), 6.91 (s, 1H), 4.39 (q, J=7.2 Hz, 2H), 4.12 (s, 3H), 1.70 (m, 4H), 1.46 (s, 3H), 1.43 (s, 3H), 1.41 (t, J=7.0 Hz, 3H,), 1.27 (m, 4H).

Ethyl 2,6-Difluoro-4-[(5-hydroxy-1,8-dimethyl-tricyclo[6.2.20$^{2,7}$]dodeca-2(7),3,5-trien-4-carbonyl)amino]benzoate (Compound 12)

Following General Procedure B, ethyl 2,6-difluoro-4-[(5-methoxy-1,8-dimethyl-tricyclo[6.2.2.0$^{2,7}$]dodeca-2(7),3,5-triene-4-carbonyl)amino]benzoate (Compound 11, 109 mg, 0.25 mmol) and boron tribromide (0.37 mg, 0.37 mmol) were reacted to produce the title compound as a white solid.

$^{1}$H NMR CDCl$_3$ δ 11.43 (s, 1H), 8.05 (s, 1H), 7.37 (s, 1H), 7.34 (s, 1H), 7.16 (s, 1H), 6.92 (s, 1H), 4.40 (q, J=7.2 Hz, 2H), 1.70 (m, 4H), 1.42 (s, 3H), 1.40 (s, 3H), 1.39 (t, J=7.0 Hz, 3H), 1.27 (m, 4H).

Ethyl 4-[(6-Bromo-5-hydroxy-1,8-dimethyl-tricyclo[6.2.20$^{2,7}$]dodeca-2(7),3,5-trien-4-carbonyl)-amino]-2,6-difluorobenzoate (Compound 13)

Following General Procedure D, ethyl 2,6-difluoro-4-[(5-hydroxy-1,8-dimethyl-tricyclo[6.2.20$^{2,7}$]dodeca-2(7),3,5-trien-4-carbonyl)amino]benzoate (Compound 12, 34 mg, 0.08 mmol) and bromine (0.004 mg, 0.08 mmol) were reacted to produce the title compound as a white solid.

$^{1}$H NMR CDCl$_3$ δ 9.12 (s, 1H), 7.61 (s, 1H), 7.39 (s, 1H), 7.36 (s, 1H), 4.40 (q, J=7.2 Hz, 2H), 1.78 (s, 3H), 1.62 (m, 4H), 1.44 (s, 3H), 1.39 (t, J=7.0 Hz, 3H), 1.27 (m, 4H).

4-[(6-Bromo-5-hydroxy-1,8-dimethyl-tricyclo[6.2.20$^{2,7}$]dodeca-2(7),3,5-trien-4-carbonyl)amino]-2,6-difluorobenzoic Acid (Conmpound 14)

Following General Procedure C, ethyl 4-[(6-bromo-5-hydroxy-1,8-dimethyl-tricyclo[6.2.20$^{2,7}$]dodeca-2(7),3,5-trien-4-carbonyl)-amino]-2,6-difluorobenzoate Compound 13, 39 mg, 0.08 mmol) and 2 M NaOH (aq) (1 mL) were reacted to yield the title compound as a white solid.

$^{1}$H NMR acetone-d$_6$ δ 10.29 (s, 1H), 7.72 (s, 1H), 7.56 (s, 1H), 7.52 (s, 1H), 1.76 (s, 3H), 1.69 (m, 2H), 1.55 (m, 2H), 1.37 (s, 3H), 1.21 (m, 4H).

What is claimed is:

1. A compound of the formula

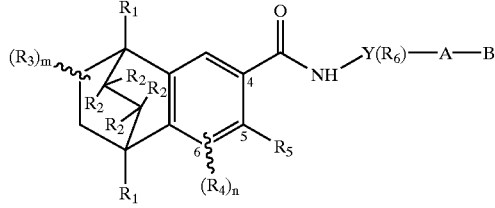

where $R_1$ is independently H, or alkyl of 1 to 6 carbons;

$R_2$ is independently H, or alkyl of 1 to 6 carbons;

$R_3$ is alkyl of 1 to 6 carbons, or halogen;

m is an integer having the values of 0 to 4;

$R_4$ independently is alkyl of 1 to 6 carbons or halogen;

n is an integer having the values of 0 to 2;

$R_5$ is H or OH;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_6$ groups; $R_6$ is halogen, alkyl of 1 to 10 carbons, fluoro substituted alkyl of 1 to 6 carbons, alkoxy of 1 to 10 carbons, or alkylthio of 1 to 10 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, or $CH_2OCH_3$, or $R_8$ is phenyl or $C_{1-6}$ alkylphenyl, $R_9$ and $R_{10}$ independently are hydrogen, an alkyl group of 1 to 10 carbons, or a cycloalkyl group of 5–10 carbons, or phenyl or $C_{1-6}$-alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2–5 carbons, or a pharmaceutically acceptable salt of said compound.

2. A compound in accordance with claim 1 wherein Y is phenyl.

3. A compound in accordance with claim 2 wherein the phenyl group is 1,4 substituted by the carbamoyl and A—B groups.

4. A compound in accordance with claim 1 wherein Y is pyridyl, thienyl or furanyl.

5. A compound in accordance with claim 1 wherein $R_1$ is H or lower alkyl of 1 to 3 carbons.

6. A compound in accordance with claim 1 wherein $R_2$ is H.

7. A compound in accordance with claim 1 wherein m is zero (0).

8. A compound in accordance with claim 1 wherein n is zero (0).

9. A compound in accordance with claim 1 wherein $R_4$ is halogen.

10. A compound in accordance with claim 9 wherein $R_4$ is bromine.

11. A compound in accordance with claim 1 wherein $R_5$ is OH.

12. A compound in accordance with claim 1 wherein $R_6$ is halogen.

13. A compound in accordance with claim 1 wherein $R_6$ is fluoro.

14. A compound in accordance with claim 1 where the A—B group represents $(CH_2)_q COOR_8$ or $(CH_2)_q COOH$ where q is 0, or a pharmaceutically acceptable salt thereof.

15. A compound of the formula

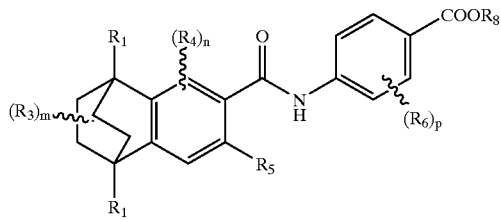

where $R_1$ is independently H, or alkyl of 1 to 3 carbons;
$R_3$ is alkyl of 1 to 6 carbons, or halogen;
m is an integer having the values of 0 to 4;
$R_4$ independently is alkyl of 1 to 3 carbons or halogen;
n is an integer having the values of 0 to 2;
$R_5$ is H or OH;
$R_6$ is halogen, alkyl of 1 to 3 carbons, fluoro substituted alkyl of 1 to 3 carbons, alkoxy of 1 to 3 carbons, or alkylthio of 1 to 3 carbons;
p is an integer having the values 0 to 2, and
$R_8$ is H, an alkyl group of 1 to 10 carbons or a pharmaceutically acceptable salt of said compound.

16. A compound in accordance with claim 15 where $R_1$ is methyl.

17. A compound in accordance with claim 15 where m is zero (0).

18. A compound in accordance with claim 15 where n is one (1) and $R_4$ is bromine.

19. A compound in accordance with claim 15 where p is one (1) or two (2) and $R_6$ is F.

20. A compound in accordance with claim 15 where $R_5$ is OH.

21. A compound of the formula

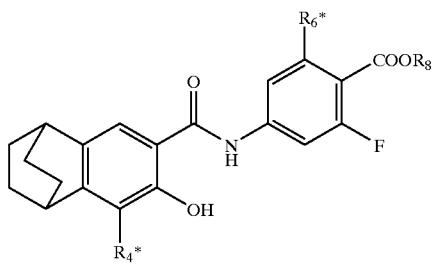

where $R_4^*$ is H or Br;
$R_6^*$ is H or F, and
$R_8$ is H, an alkyl group of 1 to 10 carbons or a pharmaceutically acceptable salt of said compound.

22. A compound in accordance with claim 21 where $R_4^*$ is H, and $R_6^*$ is H.

23. A compound in accordance with claim 22 where $R_8$ is ethyl, H, or a pharmaceutically acceptable salt of said compound.

24. A compound in accordance with claim 21 where $R_4^*$ is Br, and $R_6^*$ is H.

25. A compound in accordance with claim 24 where $R_8$ is ethyl, H, or a pharmaceutically acceptable salt of said compound.

26. A compound in accordance with claim 21 where $R_4^*$ is Br, and R is F.

27. A compound in accordance with claim 26 where $R_8$ is ethyl, H, or a pharmaceutically acceptable salt of said compound.

* * * * *

UNITED STATES PATENT AND TRADEMARK OFFICE
CERTIFICATE OF CORRECTION

PATENT NO. : 6,620,963 B1
DATED : September 16, 2003
INVENTOR(S) : Duong et al.

It is certified that error appears in the above-identified patent and that said Letters Patent is hereby corrected as shown below:

Column 3,
Line 47, "$CH_{21\ OH},\ _{CH2}OR_{11}$" should be -- $CH_2OH,\ CH_2OR_{11}$ --

Column 12,
Line 34, "(MAP)" should be -- (DMAP) --
Line 67, "14" should be -- 14 --

Column 13,
Lines 56 and 57, "Spiro" should be -- *spiro* --

Column 14,
Line 46, "O°C.," should be -- O°C, --
Line 48, "O°C." should be -- O°C --

Signed and Sealed this

Thirtieth Day of November, 2004

JON W. DUDAS
*Director of the United States Patent and Trademark Office*